(12) United States Patent
Harada et al.

(10) Patent No.: US 6,603,037 B2
(45) Date of Patent: Aug. 5, 2003

(54) ESTER COMPOUNDS

(75) Inventors: Yuji Harada, Niigata-ken (JP); Jun Hatakeyama, Niigata-ken (JP); Yoshio Kawai, Niigata-ken (JP); Masaru Sasago, Hirakata (JP); Masayuki Endo, Izumi (JP); Shinji Kishimura, Itami (JP); Kazuhiko Maeda, Tokyo (JP); Michitaka Ootani, Tokyo (JP); Haruhiko Komoriya, Kawagoe (JP)

(73) Assignees: Shin-Etsu Chemical Co., Ltd., Tokyo (JP); Matsushita Electric Industrial Co., Ltd., Osaka (JP); Central Glass Co., Ltd., Ube (JP)

( * ) Notice: Subject to any disclaimer, the term of this patent is extended or adjusted under 35 U.S.C. 154(b) by 0 days.

(21) Appl. No.: 10/305,085

(22) Filed: Nov. 27, 2002

(65) Prior Publication Data

US 2003/0100791 A1 May 29, 2003

(30) Foreign Application Priority Data

Nov. 28, 2001 (JP) ......................................... 2001-362667

(51) Int. Cl.$^7$ ................................................. C07C 69/62
(52) U.S. Cl. ........................ 560/219; 560/223; 560/192; 560/197
(58) Field of Search ................................. 560/219, 223, 560/192, 197

(56) References Cited

U.S. PATENT DOCUMENTS

| 4,491,628 A | 1/1985 | Ito et al. |
| 5,310,619 A | 5/1994 | Crivello et al. |

FOREIGN PATENT DOCUMENTS

| JP | 63-27829 A | 2/1988 |
| JP | 2-27660 B2 | 6/1990 |
| JP | 9-73173 A | 3/1997 |
| JP | 9-230595 A | 9/1997 |
| JP | 10-10739 A | 1/1998 |
| WO | WO 97-33198 | 9/1997 |

*Primary Examiner*—Alan L. Rotman
*Assistant Examiner*—Héctor M. Reyes
(74) *Attorney, Agent, or Firm*—Birch, Stewart, Kolasch & Birch, LLP

(57) ABSTRACT

Acrylic esters containing fluorine at α-position and having an alkoxymethyl group introduced into the ester side chain thereof are novel. Polymers obtained from the acrylic esters are improved in transparency, acid elimination and substrate adhesion and are used to formulate chemically amplified resist compositions for lithographic microfabrication.

2 Claims, No Drawings

ESTER COMPOUNDS

This nonprovisional application claims priority under 35 U.S.C. §119(a) on patent application Ser. No. 2001-362667 filed in JAPAN on Nov. 28, 2001, which is herein incorporated by reference.

This invention relates to novel ester compounds which are useful as a monomer to produce base polymers for use in chemically amplified resist compositions for microfabrication.

BACKGROUND OF THE INVENTION

In the drive for higher integration and operating speeds in LSI devices, the pattern rule is made drastically finer. The rapid advance toward finer pattern rules is grounded on the development of a projection lens with an increased NA, a resist material with improved performance, and exposure light of a shorter wavelength. To the demand for a resist material with a higher resolution and sensitivity, acid-catalyzed chemical amplification positive working resist materials are effective as disclosed in U.S. Pat. No. 4,491,628 and U.S. Pat. No. 5,310,619 (JP-B 2-27660 and JP-A 63-27829). They now become predominant resist materials especially adapted for deep UV lithography. Also, the change-over from i-line (365 nm) to shorter wavelength KrF laser (248 nm) brought about a significant innovation. Resist materials adapted for KrF excimer lasers enjoyed early use on the 0.30 micron process, went through the 0.25 micron rule, and currently entered the mass production phase on the 0.18 micron rule. Engineers have started investigation on the 0.15 micron rule, with the trend toward a finer pattern rule being accelerated.

For ArF laser (193 nm), it is expected to enable miniaturization of the design rule to 0.13 μm or less. Since conventionally used novolac resins and polyvinylphenol resins have very strong absorption in proximity to 193 nm, they cannot be used as the base resin for resists. To ensure transparency and dry etching resistance, some engineers investigated acrylic and alicyclic (typically cycloolefin) resins as disclosed in JP-A 9-73173, JP-A 10-10739, JP-A 9-230595 and WO 97/33198.

With respect to $F_2$ excimer laser (157 nm) which is expected to enable further miniaturization to 0.10 μm or less, more difficulty arises in insuring transparency because it was found that acrylic resins which are used as the base resin for ArF are not transmissive to light at all and those cycloolefin resins having carbonyl bonds have strong absorption. It was also found that poly(vinyl phenol) which is used as the base resin for KrF has a window for absorption in proximity to 160 nm, so the transmittance is somewhat improved, but far below the practical level.

SUMMARY OF THE INVENTION

An object of the invention is to provide a novel ester compound useful as a monomer to produce a base polymer which has a high transmittance to vacuum ultraviolet radiation of up to 300 nm, especially $F_2$ (157 nm), $Kr_2$ (146 nm), KrAr (134 nm) and $Ar_2$ (126 nm) excimer laser beams, and is useful as the base resin in a chemically amplified resist composition.

It has been found that acrylic acid esters of the general formula (1), shown below, containing fluorine at α-position and having an alkoxymethyl group introduced in the ester side chain are useful monomers from which base polymers for resist compositions, especially chemically amplified resist compositions, are prepared.

Among the approaches for increasing the transmittance of resins in proximity to 157 nm, it is believed effective to reduce the number of carbonyl groups and carbon-to-carbon double bonds. It has been ascertained that the introduction of fluorine atoms into monomeric units makes a great contribution to the transmittance improvement as well. Specifically, the inventor has discovered that polymers obtained from acrylate monomers containing fluorine at α-position as represented by the structure of formula (1) below have a high transparency in proximity to 157 nm. Since the acrylate monomers additionally have an alkoxymethyl group on the ester side chain, the polymers are drastically improved in acid elimination and substrate adhesion.

The present invention provides an ester compound of the following general formula (1).

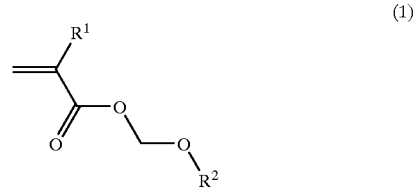

(1)

Herein $R^1$ is a fluorine atom or a straight, branched or cyclic alkyl group of 1 to 15 carbon atoms having at least one fluorine atom, and $R^2$ is a straight, branched or cyclic alkyl group of 1 to 15 carbon atoms which may be separated by an oxygen atom. Typically $R^1$ is trifluoromethyl.

DESCRIPTION OF THE PREFERRED EMBODIMENTS

The ester compounds of the present invention have the following general formula (1).

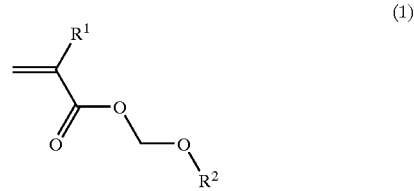

(1)

Herein $R^1$ is a fluorine atom or a straight, branched or cyclic alkyl group of 1 to 15 carbon atoms having at least one fluorine atom. $R^2$ is a straight, branched or cyclic alkyl group of 1 to 15 carbon atoms which may contain a hetero atom. Typically, the alkyl group represented by $R^2$ may be separated by an oxygen atom in the form of —O—.

Specifically, suitable alkyl groups include, but are not limited to, methyl, ethyl, n-propyl, isopropyl, n-butyl, isobutyl, tert-butyl, pentyl, cyclopentyl, hexyl, cyclohexyl, octyl, decyl, and dodecyl. Suitable alkyl groups having a fluorine atom(s) include the foregoing alkyl groups in which some or all of the hydrogen atoms are substituted with fluorine atoms.

Illustrative examples of the ester compounds of the invention are given below, but the invention is not limited thereto.

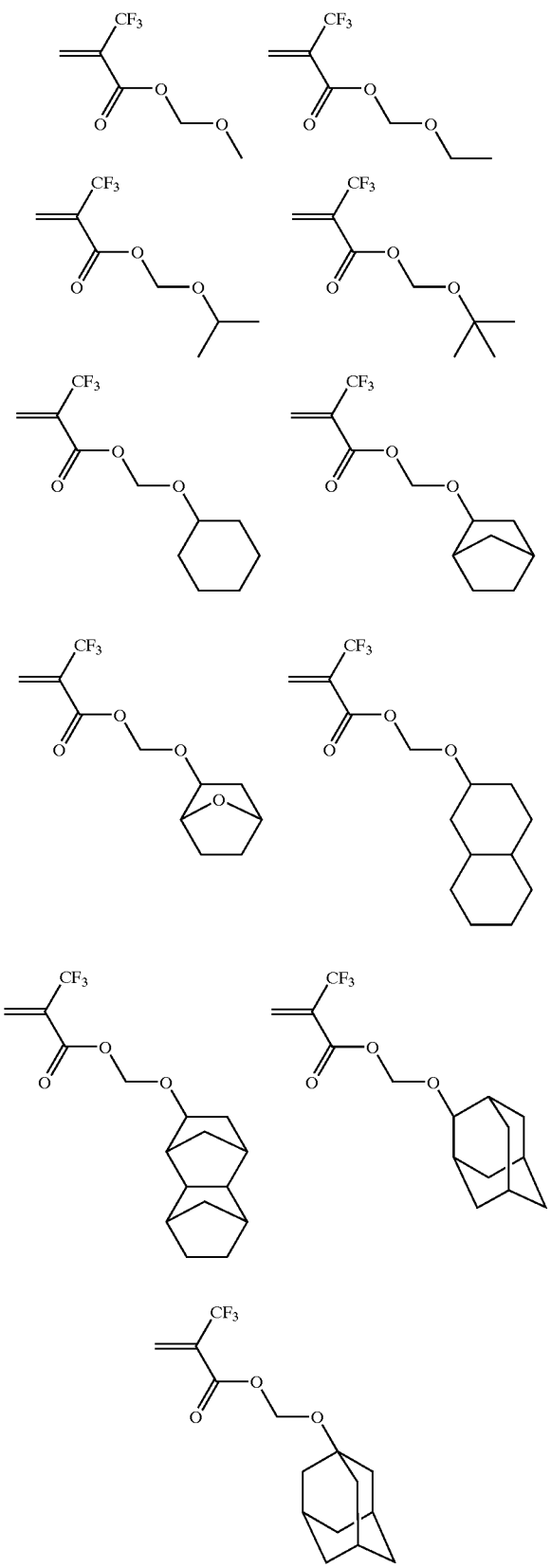

The ester compounds of the invention can be prepared, for example, by the following process, but the invention is not limited thereto.

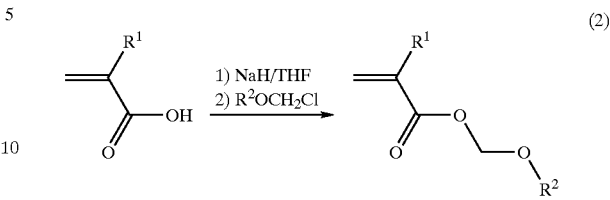

Herein, $R^1$ and $R^2$ are as defined above. The reaction readily proceeds under well-known conditions. In one preferred procedure, equimolar amounts of an acrylic acid substituted at a-position and sodium hydride are reacted in a solvent such as tetrahydrofuran. Then a chloromethyl alkyl ether in an equimolar amount to the acrylic acid is added dropwise, followed by reaction at room temperature. By conventional post treatment and distillation, the product is isolated.

The ester compounds of the invention are useful as a monomer for the production of polymers. The polymers obtained therefrom are used as a base resin to formulate resist compositions which are improved in transparency, acid elimination and substrate adhesion and thus useful in micropatterning with electron beam and deep UV, especially $F_2$ excimer laser beam.

EXAMPLE

Example of the invention is given below by way of illustration and not by way of limitation.

Synthesis Example

A typical ester compound within the scope of the invention, methoxymethyl α-trifluoromethylacrylate was synthesized by the following procedure.

A three-necked flask was charged with 18.8 g of sodium hydride, which was washed with hexane three times in a nitrogen stream. Then 60.0 g of α-trifluoromethylacrylic acid was added dropwise little by little to the tetrahydrofuran solution at room temperature, following which the solution was stirred for one hour at room temperature. Then 34.4 g of chloromethyl methyl ether was added to the flask, followed by 12 hours of reaction at room temperature. Conventional post treatment and distillation (boiling point 92° C./11.7 kPa) were carried out for purification, obtaining 47.6 g of methoxymethyl α-trifluoromethylacrylate. The yield was 60%.

$^1$H-NMR (CDCl$_3$, 270 MHz): δ 3.51 (s, 3H), 5.40 (s, 2H), 6.49 (m, 1H), 6.79 (m, 1H) FT-IR (NaCl): 3010, 2966, 1743, 1456, 1407, 1361, 1346, 1245, 1213, 1170, 1147, 1110, 1085, 1068, 997, 929, 875, 811 cm$^{-1}$.

Japanese Patent Application No. 2001-362667 is incorporated herein by reference.

Reasonable modifications and variations are possible from the foregoing disclosure without departing from either the spirit or scope of the present invention as defined by the claims.

What is claimed is:

1. An ester compound of the following general-formula (1):

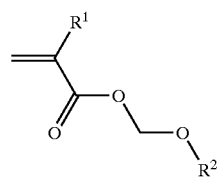

(1)

wherein $R^1$ is a fluorine atom or a straight, branched or cyclic alkyl group of 1 to 15 carbon atoms having at least one fluorine atom, and $R^2$ is a straight, branched or cyclic alkyl group of 1 to 15 carbon atoms which may be separated by an oxygen atom.

2. The ester compound of claim 1 wherein $R^1$ is trifluoromethyl.

* * * * *